United States Patent
Wang et al.

(10) Patent No.: US 6,767,830 B2
(45) Date of Patent: Jul. 27, 2004

(54) BR2SBCH3 A SOLID SOURCE ION IMPLANT AND CVD PRECURSOR

(75) Inventors: Ziyun Wang, New Milford, CT (US); Chongying Xu, New Milford, CT (US); Thomas H. Baum, New Fairfield, CT (US); Michael A. Todd, Phoenix, AZ (US); Niamh McMahon, Binnirgen (IE)

(73) Assignee: Advanced Technology Materials, Inc., Danbury, CT (US)

( * ) Notice: Subject to any disclaimer, the term of this patent is extended or adjusted under 35 U.S.C. 154(b) by 0 days.

(21) Appl. No.: 10/213,669

(22) Filed: Aug. 7, 2002

(65) Prior Publication Data

US 2004/0029367 A1 Feb. 12, 2004

(51) Int. Cl.$^7$ .................. H01L 21/44; C23C 14/26; C07F 9/90
(52) U.S. Cl. ................ 438/681; 427/523; 427/587; 427/593; 438/604; 556/70
(58) Field of Search ............... 556/70; 438/604, 438/681; 427/523, 587, 593

(56) References Cited

PUBLICATIONS

Malish et al., Chem. Ber., vol. 108, pp. 700–715 (1975).*
L. Wang, et al., Semiconductor International, Next Generation Dopont Development and Characterization, Oct. 1, 1998.

H. Althaus, et al., Organometallics 2001, 20, 586–589, Syntheses and Chemistry of Methylantimony and Methylbismuth Dihalides: An Extended Two–Dimensional Framework in the Crystal Structure of...

Alan Berry, "Encyclopedia of Inorganic Chemistry" vol. 1 "Antimony Organometallic Chemistry" p. 176–190.

Ates, Mustafa et al., "Alkylantimondichloride und—bromide", *Journal of Organometallic Chemistry*, 364 (1989) pp. 67–71.

Breunig, Hans Joachim et al., "Strukturen und Reaktionen von Methylantimondihalogeniden und Versuche zur Darstellung von Methylantimon" *Journal of Organometallic Chemistry*, 470 (1994) pp. 87–92.

* cited by examiner

*Primary Examiner*—Porfirio Nazario-Gonzalez
(74) *Attorney, Agent, or Firm*—William F. Ryann; Steven J. Hultquist; Margaret Chappuis

(57) ABSTRACT

A volatile solid-source novel antimony precursor, $Br_2SbCH_3$, that may be utilized in semiconductor processing chambers for depositing antimony on a substrate by deposition methods, e.g., chemical vapor deposition, ion implantation, molecular beam epitaxy, diffusion and rapid thermal processing. The novel antimony compound of the invention is synthesized by combining tribromide antimony with trimethylantimony under heating conditions that form a $Br_2SbCH_3$ crystalline product.

13 Claims, 2 Drawing Sheets

$^{13}$C NMR SPECTRUM OF $CH_3SbBr_2$ in $CDCl_3$ $^1$H NMR OF $Br_2SbCH_3$ $(C_6D_6)$

BR2SBCH3 A SOLID SOURCE ION IMPLANT AND CVD PRECURSOR

BACKGROUND OF INVENTION

1. Field of the Invention

The present invention relates to a novel solid source antimony precursor, and more particularly, to $Br_2SbCH_3$ and method of synthesizing same for use in ion implantation and deposition.

2. Description of the Related Art

The reduction in critical dimensions necessary for continued gains in dynamic random access memory (DRAM) circuit density will require a number of fundamental changes from current practice, relative to the techniques and source materials employed in current manufacturing practice. As geometries of such DRAM devices decrease below 0.35 micrometer, a corresponding reduction is necessary in the size of p/n dopant layer thicknesses and in the associated dopant concentrations.

The mobility of lightweight p-type and n-type dopants is too high, even with reduced thermal budgets, to accommodate the increased stringency of future implant requirements. Thus, it will be necessary to develop dopants that can be utilized in very shallow p/n layers. This implies that traditional dopants such as boron (p-type) and phosphorus (n-type) will have to be replaced due to their high mobility in silicon (which results in a breakdown of the junction, even with reduced thermal budgets).

Dopants with significantly greater size and mass, will need to be used to improve control of ion throughput and to reduce channeling effects in the fabricated structures. A logical choice for an n-type dopant is antimony, due to its greater size and mass, that provide superior diffusion characteristics relative to traditional implant species. These properties make it possible to use lower implant energies and more advantageous geometries when depositing the shallow p/n junctions that are critical to DRAM storage density increases.

Currently solid species, such as $Sb_2O_3$ and $SbF_3$ are used to generate ion beams for ion implantation but have been found to be problematic. For example, $Sb_2O_3$ requires high temperatures to volatize, leading to particle formation from recondensation or entrainment within the ion implanter. The addition of fluorine may cause additional diffusion of which often results in contamination of the well region and loss of threshold voltage control in the resulting devices.

Chemical vapor deposition (CVD) offers a low-cost, high throughput approach to device manufacturing. However, a lack of suitable, low temperature CVD precursors has hindered its widespread applicability. This is particularly true for Sb-based heterostructures that display important optoelectronic and electronic properties, including InSb, InGaSb, InAsSb, GaAlSb and InSbBi. Unfortunately, current Sb CVD sources require processing temperatures in excess of 460° C. to achieve precursor decomposition and useful film growth rates. Volatile and thermally stable Sb precursors would facilitate the chemical vapor deposition of antimonide thin-films, as required for the large scale, controlled production of antimonide based lasers, detectors and microelectronic sensors.

Thus, suitable volatile antimony precursors are currently unavailable. Accordingly, the art is in need of new source compositions of antimony for ion implant and CVD applications.

SUMMARY OF THE INVENTION

The present invention relates to novel antimony compounds and method of synthesizing same. The novel antimony compounds of the invention may have the formula:

$X_2SbCH_3$ wherein each X is a halogen and independently selected from the group consisting of F, Cl, Br and I, and preferably the halogen is Br. It has been expectedly discovered that the novel antimony compounds, having only one carbon molecule, exhibit high volatility.

In another aspect, the invention relates to a method of synthesizing the antimony compounds of the invention comprising:

combining a trihalide antimony compound with trimethylantimony;

heating the trihalide antimony compound and trimethylantimony at a temperature of from 30° C. to about 90° C. for the a sufficient amount of time to at least melt the trihalide antimony compound and to form a $X_2SbCH_3$ product; and purifying the $X_2SbCH_3$ to form a crystalline product.

Preferably, the trihalide antimony compound and the trimethylantimony compound are combined and heated without a solvent at a temperature from about 60° to 75° C.

In yet another aspect, the invention relates to a method of depositing antimony on a substrate from an antimony-containing precursor therefor, comprising using as a precursor an antimony molecule of the formula:

$X_2SbCH_3$ wherein each X is a halogen independently selected from the group consisting of F, Cl, Br and I, and preferably the halogen is Br.

In such a method, the antimony compound of the invention may be deposited by a deposition process including, but not limited to, chemical vapor deposition, assisted chemical vapor deposition (e.g., laser, light, plasma, ion, etc.), ion implantation, molecular beam epitaxy, diffusion and rapid thermal processing.

Other aspects and features of the invention will be more fully apparent from the ensuing disclosure and appended claims.

DETAILED DESCRIPTION OF THE INVENTION, AND PREFERRED EMBODIMENTS THEREOF

Figure 1:
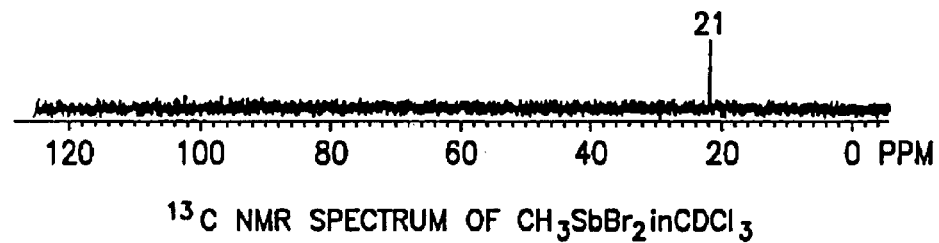
FIG. 1 shows a $^{13}C$ NMR spectrum of $Br_2SbCH_3$ evidencing a single resonance at about 21 ppm ($CDCl_3$).

The present invention is based on a novel antimony molecule, dibromomethylstibine, a volatile solid-source antimony precursor that may be utilized in semiconductor processing chambers, such as ion implanters and CVD deposition chambers.

The antimony molecule of the invention is a light yellow crystalline solid that readily transports under vacuum at room temperature. The antimony molecule which includes a single carbon atom will help to minimize the amount of contamination found within a processing chamber as a result of decomposition the antimony compound. In addition, the presence of Br within the molecule may also result in "resublimation" of any Sb deposits that may form within the ion implant chamber because $SbBr_3$ is known to boil at 288° C., but sublimes at lower temperatures under vacuum. Further, it is contemplated by the inventors that any excess Br will be eliminated from a processing chamber.

The antimony source reagents of the invention may be employed to deposit antimony on a substrate, e.g., by a process such as chemical vapor deposition, assisted chemical vapor deposition (e.g., laser, light, plasma, ion, etc.), ion implantation, molecular beam epitaxy, or rapid thermal processing.

The synthesis of the novel antimony compound of the invention may be effected by reacting the antimony compound $Sb(CH_3)_3$ with $SbX_3$ to yield the $X_2SbCH_3$. Preferably the reaction product is formed as follows:

$$Sb(CH_3)_3 + 2SbBr_3 = 3Br_2SbCH_3 \tag{a}$$

Alternatively, the antimony compound $Br_2SbCH_3$ of the invention may be formed from the corresponding halide $SbX_3$ by reacting same with $LiCH_3$ as follows:

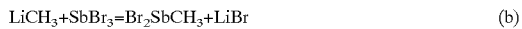

$$LiCH_3 + SbBr_3 = Br_2SbCH_3 + LiBr \tag{b}$$

The reaction described in equation (a) is preferred for several reasons including the fact that the reaction may be performed without a solvent thereby resulting in a reduced reaction cost and an easier workup and purification. The product produced by the reaction described in equation (a) is isolated via vacuum distillation or vacuum sublimation as a light yellow crystalline material.

The novel antimony compounds of the invention can be prepared by methods described herein. Specifically, a trihalide antimony compound is reacted with at least a stoichiometric amount of trimethyl antimony while heating the mixture from about 30° C. to about 90° C. for a sufficient amount of time to at least melt the trihalide antimony compound. Preferably, the trihalide antimony compound and the trimethylantimony compound are combined and heated without a solvent at a temperature from about 60° to 75° C. and the reactor is under inert nitrogen gas protection. The heating of the reaction mixture is preferably continued for at least one hour, and more preferably, for about four to ten hours. The temperature and pressure within the reaction vessel may be within a range to maintain the reaction in a liquefied state until completion. Alternatively, a condenser may be used and the reaction run at atmospheric pressures. After completion of the reaction, the formed products are easily purified by vacuum distillation or vacuum sublimation.

Figure 3:
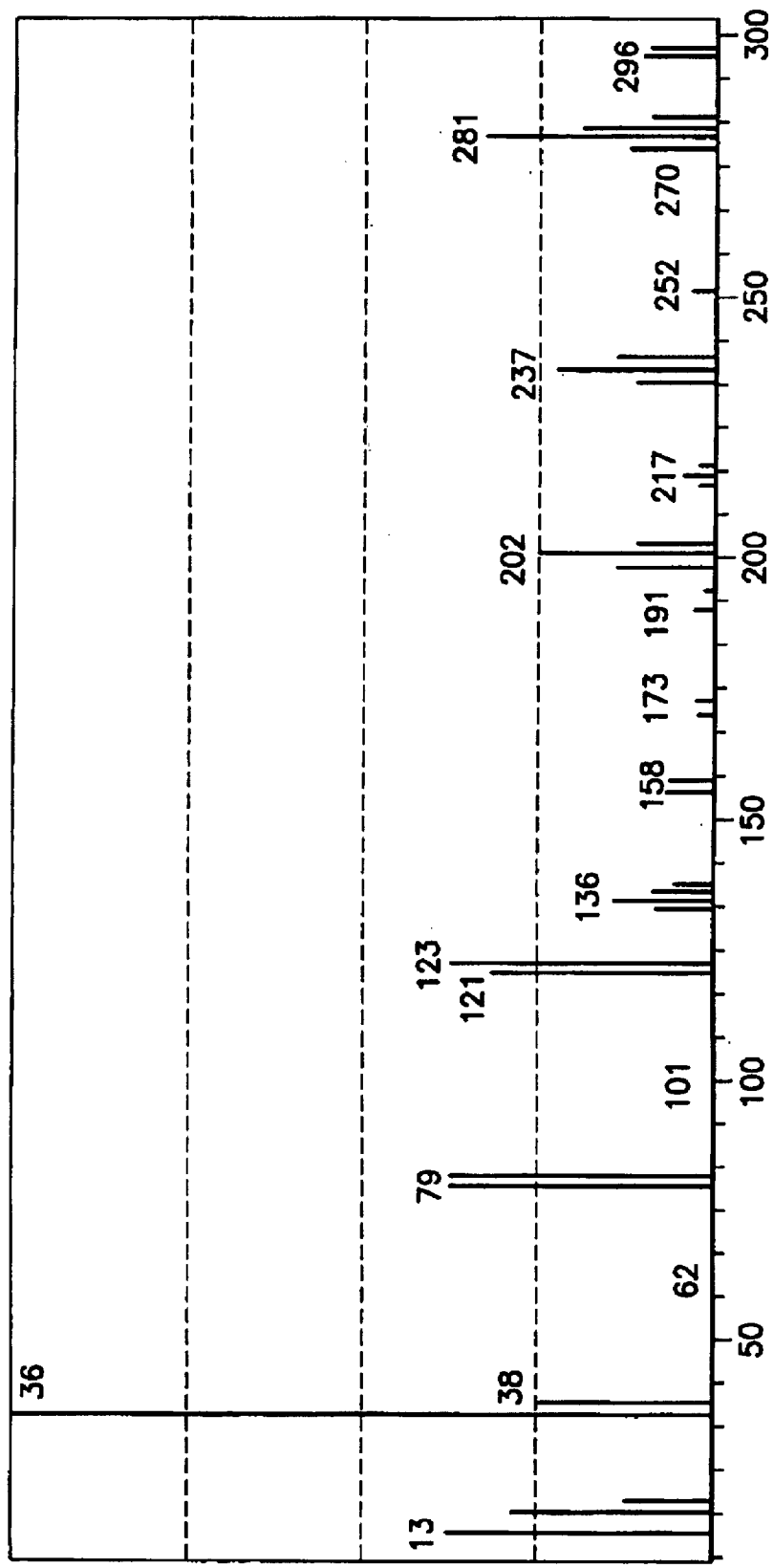
FIG. 3 shows an Electron Impact Mass Spectrum of $Br_2SbCH_3$ showing peaks arising from $^{121}Sb^+$ and $^{123}Sb^+$.

The novel solid antimony compounds of the invention are useful for ion implantation and chemical vapor deposition. For example, the novel antimony compounds of the invention may be employed as precursors for ion implantation that is a well-known and widely used process for injecting atoms into a solid material to selected depths and concentrations in selected areas. As shown in FIG. 3, the Electron Impact Mass Spectrum of $Br_2SbCH_3$ shows peaks arising from $^{121}Sb^+$ and $^{123}SB^+$ which is indicative that the novel antimony compound can serve as a good ion implantation source.

Interestingly, because of the volatility of the novel antimony compounds (at or slightly above room temperature) it is possible to deliver to the implanter the vaporized antimony compound of the invention without the use of a heated crucible. For example, the vapor pressure of Br2SbMe may be between about 150 mTorr and about 250 mTorr at about 25° C. and between about 550 mTorr and about 650 mTorr at about 45° C. Further, it is contemplated that the need for heated lines in the introduction system of the implanter can be reduced or completely eliminated thereby reducing the overall operation cost of using the novel antimony compounds.

Since the equipment and methods of ion implantation are so thoroughly described and widely used in the semiconductor industry, those skilled in the art are familiar with these methods and devices.

Briefly, ion implant accelerators used in ion implantation are similar to isotope separators but typically have an added acceleration stage and field controls for precisely locating the beam of ions and controlling the energy and flux of the beam of ions to cause the desired penetration and concentration. Atoms of the selected chemical element to be ionized are ionized by collisions with electrons in an electrical discharge in a gas at low pressure and pass through an orifice into a high-vacuum region where they are accelerated by an electric field to an intermediate energy, typically from 10 to 30 KeV, where they are analyzed by a magnetic field based upon the e/m ratio, i.e. the ratio of electronic charge over mass. The selected ion beam passes through an analyzer slit, and the ions are accelerated to the desired energy, and the beam passes through a refocusing field, typically a quadrupole lens, is deflected by a scanner system, and collimated by a defined aperture and allowed to strike the target. When the ions penetrate the target lattice, they lose energy through collisions with lattice atoms and come to rest as part of the target. There are, of course, a large number of variations between specific ion implant systems but the foregoing principles apply generally to ion implant processes.

Further the novel solid antimony compounds of the invention can be dissolved or suspended in a compatible solvent medium and be employed in liquid delivery chemical vapor deposition, wherein the solution or suspension is vaporized and antimony is deposited on a substrate in a CVD reactor from the vapor phase of the precursor material.

The antimony compounds of the invention have broad use as antimony sources for the CVD of antimonides and in the ion implantation of $Sb^+$ in the semiconductor industry, e.g., for the fabrication of III–V compound semiconductors, and for forming thin-film, long wavelength infrared detecting materials such as InSb, InAsSb, InGaSb, InSbBi and InAsSbBi.

Additionally, the antimony compounds of the invention may be utilized to form InSb as an advantageous material for high speed devices due to its high electron mobility and maximum electron drift velocity. The growth of high-quality InSb epitaxial layers may be carried out with antimony compounds of the present invention that decompose cleanly at low processing temperatures and thereby limit diffusion and melting of InSb (melting point of about 525° C.).

In this respect, the antimony compounds of the invention achieve a substantial advance in the art over traditional alkyl-antimony precursors. Such traditional precursors are not useful for the growth of high quality, crystalline InSb epitaxial layers which possess abrupt interfaces, because of the high processing temperatures required for such traditional source reagents.

Antimony compounds of the invention may be employed as precursors for depositing antimony in the fabrication of other devices, e.g., infrared optoelectronic devices such as Type-II quantum well lasers based on superlattice LED heterostructures (with quantum well structures comprised of materials such as InAsSb with cladding layers of InPSb and AlAsSb) to provide mid-infrared range emissions, chemical sensor systems, infrared military counter-measure devices, mid-infrared lasers involving active regions comprised of InAs/InGaSb/InAs with lattice matching to AlSb cladding layers, and devices for the detection of methane and carbon dioxide (with antimonide materials providing emission at wavelengths critical for the detection of methane (3.3.mu.m) and carbon dioxide (4.2 .mu.m)).

Chemical beam epitaxy is another fabrication technique which can benefit from the present invention. The chemicals in chemical beam epitaxy are admitted into a high vacuum growth chamber and impinge directly line of sight onto a heated substrate surface in the form of a molecular beam. In chemical beam epitaxy the desired reactant chemicals, metals such as Sb as well as Ga, Al and In are separately disassociated by heat and their respective vapor pressures drive them through a targeting device in the evacuated reaction chamber to the selected target for appropriate reaction.

The final specific technique to mention here which is benefited by the present invention is diffusion. In diffusion the diffusion source is typically heat decomposed over the substrate to be treated while the substrate itself is also heated. The heating process allows the source elements to diffuse into and diffuse by migration within the substrate to the appropriate lattice location. The substrate can be any electronic material such as glass, silicon, polysilicon, single crystal silicon or various specific electronic structures in such substrates.

The features and advantages of the present invention are more fully shown by the following non-limiting examples.

EXAMPLE 1

In a nitrogen filled dry glovebox (Vacuum Atmospheres Model HE-553-4) 100 g (277 mmoles) of $SbBr_3$ and 23.1 g (138 mmoles) of $Sb(CH_3)_3$ were added to a flask which was equipped with a magnetic stirrer. The flask was removed from the dry glovebox and connected to a condenser while under nitrogen gas flow. The mixture was gently heated to about 70° C. in an oil bath. In about one hour, substantially all of the solid $SbBr_3$ was melted and the reaction mixture was a dark color. The temperature was maintained at 70° C. overnight. The flask was wrapped with aluminum foil to prevent any additional reaction due to any light sensitivity of the reaction mixture. The reaction mixture was cooled to room temperature and the product solidified to a crystalline product. Vacuum sublimation was used to purify the product which was a light yellow crystalline product. After sublimation, the product yield of $Br_2SbCH_3$ was about 80%.

Figure 2:
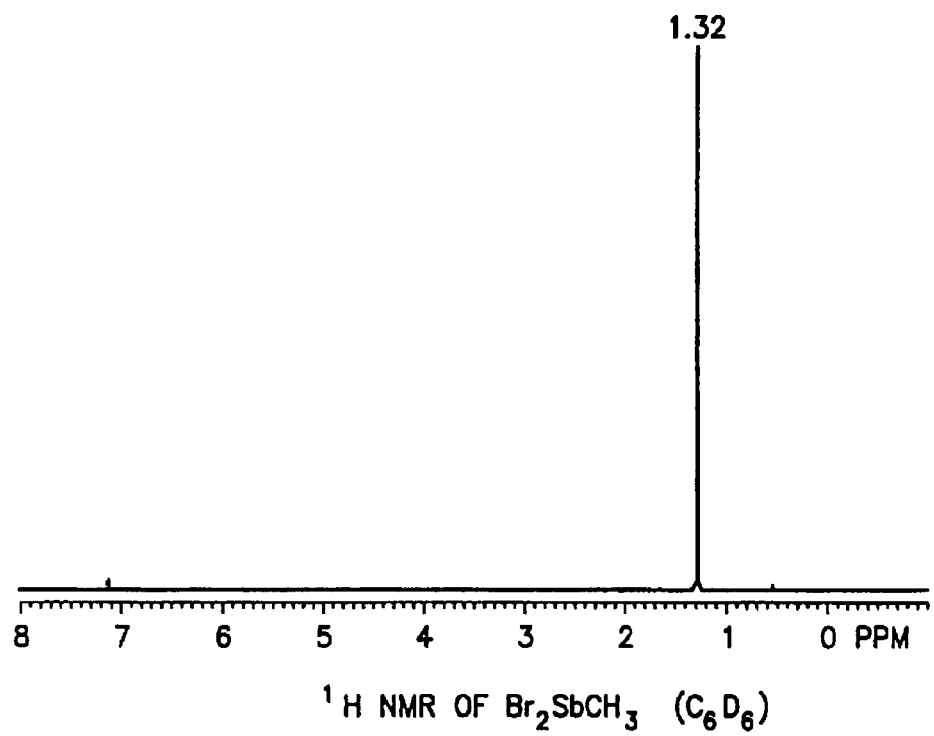
FIG. 2 shows a $^1H$ NMR spectrum of $Br_2SbCH_3$ evidencing a single resonance at about 1.32 ppm ($C_6D_6$).

The final product was characterized by Nuclear Magnetic Resonance ($^1H$ NMR) in both $CDCl_3$ and $C_6D_6$ solvent to determine conversion of reactants to the novel antimony compound of the invention. The reaction product showed a single resonance peak at about 2.19 ppm (in $CDCl_3$) and about 1.32 ppm (as shown in FIG. 2 in $C_6D_6$) both of which was assigned to the proton of the methyl group in $Br_2SbCH_3$. Further, characterization by $^{13}C$ NMR showed a single resonance peak at about 21 ppm (FIG. 1 in $CDCl_3$). The melting temperature of the novel antimony compound was determined by a Simultaneous Thermal Analyzer and found to be around 48° C.

EXAMPLE 2

Compatibility studies were conducted to explore the reactivity of the novel antimony compounds of the invention towards delivery and reaction container materials. In three Schlenk flasks, $Br_2SbCH_3$, was mixed with a) a piece of aluminum foil (sample A); b) none (sample B); and c) a piece of stainless steel (sample C). All three samples were heated at 65° C. for 15 hours. It was found that $Br_2SbCH_3$ reacted with aluminum (sample A) and formed black solid metal material. There were no visible changes with samples B and C which was confirmed by NMR studies (not included). Therefore, it was concluded that aluminum reacts with the novel antimony compound $Br_2SbCH_3$ and aluminum containers or introduction tubing systems should not be used with the $Br_2SbCH_3$ compound. Preferably containers and transference systems are fabricated of stainless steel.

What is claimed is:

1. A method of n-type doping of silicon epitaxial or polycrystalline material with an antimony compound of the formula:

$X_2SbCH_3$ wherein each x is a halogen independently selected from the group consisting of F, Cl, Br and I.

2. The method according to claim 1, wherein the halogen is bromine.

3. A method for depositing antimony on a substrate with an antimony compound of the formula:

$X_2SbCH_3$ wherein each X is a halogen independently selected from the group consisting of F, Cl, Br and I.

4. The method according to claim 3, wherein the halogen is bromine.

5. The method according to claim 4, wherein the method for depositing antimony is selected from the group consisting of: chemical vapor deposition, ion implantation, molecular beam epitaxy, diffusion and rapid thermal processing.

6. The method according to claim 5, wherein the method for depositing antimony is ion implantation.

7. A method for synthesizing an antimony compound of the formula:

$X_2SbCH_3$ wherein each X is a halogen independently selected from the group consisting or F, Cl, Br and I, the method comprising:

(a) combining a trihalide antimony compound with trimethylantimony;

(b) heating the trihalide antimony compound and trimethylantimony at a temperature from 30° C. to about 90° C. for the a sufficient time to at least melt the trihalide antimony compound and form the $X_2SbCH_3$ product; and (c) purifying the $X_2SbCH_3$ product to form a crystalline $X_2SbCH_3$ product.

8. The method according to claim 7, wherein the X is bromine.

9. The method according to claim 8, wherein the trihalide antimony compound is tribromide antimony.

10. The method according to claim 9, wherein the heating temperature is about 70° C.

11. The method according to claim 10, wherein the tribromide antimony compound and trimethylantimony mixture are heated for at least four hours.

12. The method according to claim 9, wherein the trihalide antimony compound and trimethylantimony are combined and heated without a solvent.

13. The method according to claim 9, wherein the $Br_2SbCH_3$ product is purified by vacuum sublimation.

* * * * *